United States Patent [19]

Jennings

[11] Patent Number: 5,016,468
[45] Date of Patent: May 21, 1991

[54] METHOD AND APPARATUS FOR THE DETERMINATION OF MOISTURE IN MATERIALS

[75] Inventor: Thomas A. Jennings, Bala Cynwyd, Pa.

[73] Assignee: T. A. Jennings Associates, Inc., Bala Cynwyd, Pa.

[21] Appl. No.: 333,761

[22] Filed: Apr. 5, 1989

Related U.S. Application Data

[63] Continuation-in-part of Ser. No. 177,634, Apr. 6, 1988 abandoned.
[51] Int. Cl.$^5$ .................. G01N 7/16; G01N 25/56
[52] U.S. Cl. .................................................. 73/73
[58] Field of Search .............. 73/73, 76, 29, 64.2, 73/861.53, 861.62, 863.11; 374/54

[56] References Cited

FOREIGN PATENT DOCUMENTS 429324 10/1974 U.S.S.R. .................................. 73/76
2026704 2/1980 United Kingdom .............. 73/861.53

OTHER PUBLICATIONS

D. Edwards, Jr., "Heat of Vaporazation Spectrometer", *Journal of Vacuum Science Technology*, 16(2), Mar.-/Apr. 1979, pp. 695–697.
Richard Ash et al., "Apparatus and Method for Measuring Sorption, . . . " *J. Phys. E. Sci. Instrum.*, vol. 11, 1978, pp. 262–264.
Louis Rey, "Fundamental Aspects of Lyophilization", *Aspects Theoriques et Industriels de la Lyophilisation*, pp. 24–43.
L. G. Beckett, "The Effects of Residual Moisture in Frozen-Dried Materials, and Its Measurement", *Biological Applications of Freezing and Drying*, Apr. 1975, pp. 285–301.

*Primary Examiner*—William A. Cuchlinski, Jr.
*Assistant Examiner*—W. Morris Worth
*Attorney, Agent, or Firm*—William H. Murray; Frank M. Linguiti

[57] ABSTRACT

A method and apparatus for determining the moisture in materials is provided. The apparatus allows the accurate determination of moisture in a sample as small as 1 mg with a sensitivity of less than 1 microgram of moisture. The apparatus includes a vacuum chamber which can be cooled to below $-150°$ C. or heated to about $100°$ C. The vacuum chamber is connected in series with a moisture trap which can be cooled to below $-150°$ C. The moisture trap is connected in series with a combination of mechanical and diffusion vacuum pumps capable of reducing the pressure in the apparatus to below $1 \times 10^{-5}$ Torr. A sample is placed in the vacuum chamber, cooled to below $-150°$ C., the apparatus is evacuated to a pressure of below $1 \times 10^{-5}$ Torr by the vacuum pumps. Thereafter, the moisture trap is cooled to below $-150°$ C. while the sample is heated to about $100°$ C. to transfer moisture from the sample to the trap. When the transfer of moisture from the sample to the moisture trap is completed, as indicated by a stabilization of pressure with the apparatus, the moisture trap is isolated, heated and the change in pressure directly indicates the amount of moisture removed from the sample. Alternatively, the apparatus can include flow rate determining means oriented between the vacuum chamber and the moisture trap to determine the flow rate of moisture from the sample to the moisture trap for a given sample temperature.

42 Claims, 3 Drawing Sheets

METHOD AND APPARATUS FOR THE DETERMINATION OF MOISTURE IN MATERIALS this is a continuation-in-part of application Ser. No. 177,634, filed Apr. 6, 1988, now abandoned.

FIELD OF THE INVENTION

The present invention provides a method and apparatus for determining the moisture content of a solid or gas. More specifically, the present invention provides a method and apparatus for measuring accurately a relatively small amount of water in relatively small samples, such as pharmaceuticals, biological products or microcircuits.

BACKGROUND OF THE INVENTION

The measurement of the amount of water in a solid or gas system is often considered an easy test to perform. However, the accurate measurement of relatively small amounts of water or the measurement of the amount of a water in a relatively small sample is difficult to achieve. The determination of the amount of water in a small sample is of particular importance in industries which produce pharmaceutical products, biological products or microchips, as well as the transportation of materials such as natural gas. In all of these areas, moisture content can affect the shelf life biological activity or the equipment employed during transportation and handling.

A number of assay methods are known which can determine the moisture content of a sample. However, the known assay methods are subject to variation in results and are unable to accurate assay the relatively small amounts of moisture in relatively small samples. Often, due to the sensitivity limitations of the assay method, a number of samples must be combined and the resulting measurement is only an estimated average of the moisture actually presented in each individual sample.

The oldest method for ascertaining the moisture content of a material is the loss in weight method. In the loss in weight method, a material sample, typically from 300 to 500 mg, is placed in a vacuum desiccator containing a desiccant such as phosphorous pentoxide maintained at ambient temperatures. The pressure in the desiccator is reduced to less than 1 Torr and the sample weighed at various time intervals until a constant weight is achieved. The loss in weight is attributed to that of the moisture in the materials. Difficulties arise due to the requirement that a sample of from about 300 to 500 mg be employed in order to provide an acceptable margin of error as well as the possibility of inaccurate weighing measurements, lack of effectiveness of the desiccant and problems of controlling moisture changes in the sample during the actual weighing process. Also, the loss in weight technique is not generally suitable for determining the moisture content of gases.

Another method for determining moisture content is commonly referred to as the Karl Fischer method. This method has been automated for routine use in an apparatus available from a number of sources. This method involves the solubility of the sample in methanol and a reaction and titration with an iodine based reagent. Automated machines typically employ a conductometric endpoint detection circuit. The volume of the sample required and the dryness of the extractant limit the lower detection limits to moisture values to from 5 to 10 parts per million. Typical commercial autotitrators which measure water by this method have an accuracy of about +or −10 micrograms of water. Thus, relatively large samples must be employed in order that the experimental error inherent in the process be held within acceptable limits.

An electrolysis method of moisture measurement is also known. The electolysis method is often referred to as the Du Pont method. In this method, the sample is placed in a chamber and gas such as dry nitrogen is passed over the sample. The water vapor from the sample is carried to an analytical chamber by the dry gas where the moisture reacts with a film of concentrated phosphorous pentoxide to form phosphoric acid. The phosphoric acid is quantitatively electrolized by electrodes embedded in the film. The electrolitic current is directly proportional to the mass flow rate of water through the cell. This method cannot be employed for a gas stream that may at times reach saturation. Also, hydrocarbons in the sample may coat the surface in the analytical chamber resulting in inaccurate readings.

The vapor pressure method is also a known method for determining the moisture content of a sample. In the vapor pressure method, a sample is placed in a flask connected to a vacuum pump by a U-shaped vapor trap. The vapor trap is cooled to a temperature of approximately $-50°$ C. by a dry ice in alcohol mixture. As the system is evacuated by a vacuum pump, water vapor from the sample is collected in the trap. The vapor trap is then isolated and allowed to warm to ambient temperatures. The increase in pressure is a measurement of the moisture removed from the sample. With this process, inaccurate results may be obtained due to the water vapor passing through the trap without condensing. This is especially so at higher pressures where gas flow is viscous rather than molecular. Also, at the temperature of dry ice and alcohol of approximately $-55°$ C., the vapor pressure of water vapor of ice is approximately 29 Torr. Thus, sublimation of the ice formed in the trap may result in water vapor being lost through the vacuum pump resulting in an inaccurate determination.

SUMMARY OF THE INVENTION

The present invention provides a method and apparatus for determining the moisture content of a sample which provides accurate results even with small sample sizes and when small amounts of moisture are present. The apparatus and method of the present invention first cools a sample in a vacuum chamber to a temperature lower than $-150°$ C. and preferably to $-195°$ C. as with liquid nitrogen. Thereafter, the vacuum chamber is connected to a vacuum pump by a vapor trap and the pressure is reduced to less than $1 \times 10^5$ Torr. The moisture trap is then cooled to less than $-150°$ C. and the vapor chamber containing the sample heated. The moisture from the sample is collected in the trap which is then isolated. The isolated trap is warmed and the increase in pressure directly relates to the amount of water in the sample. Because the sample is first cooled to an extremely low temperature, moisture loss during evacuation is effectively eliminated. Also, moisture loss is controlled by employing extremely low temperatures and pressures where gas flow is molecular rather than viscous so that the moisture trap operates such more efficiently. The apparatus may also include means of determining the rate of moisture release from the sample to aid in determining when moisture release is complete, and also, to determine whether the moisture being released is surface moisture or chemically bonded moisture. A method of calibrating the apparatus is also provided.

DESCRIPTION OF THE PREFERRED EMBODIMENT

Figure 1A:
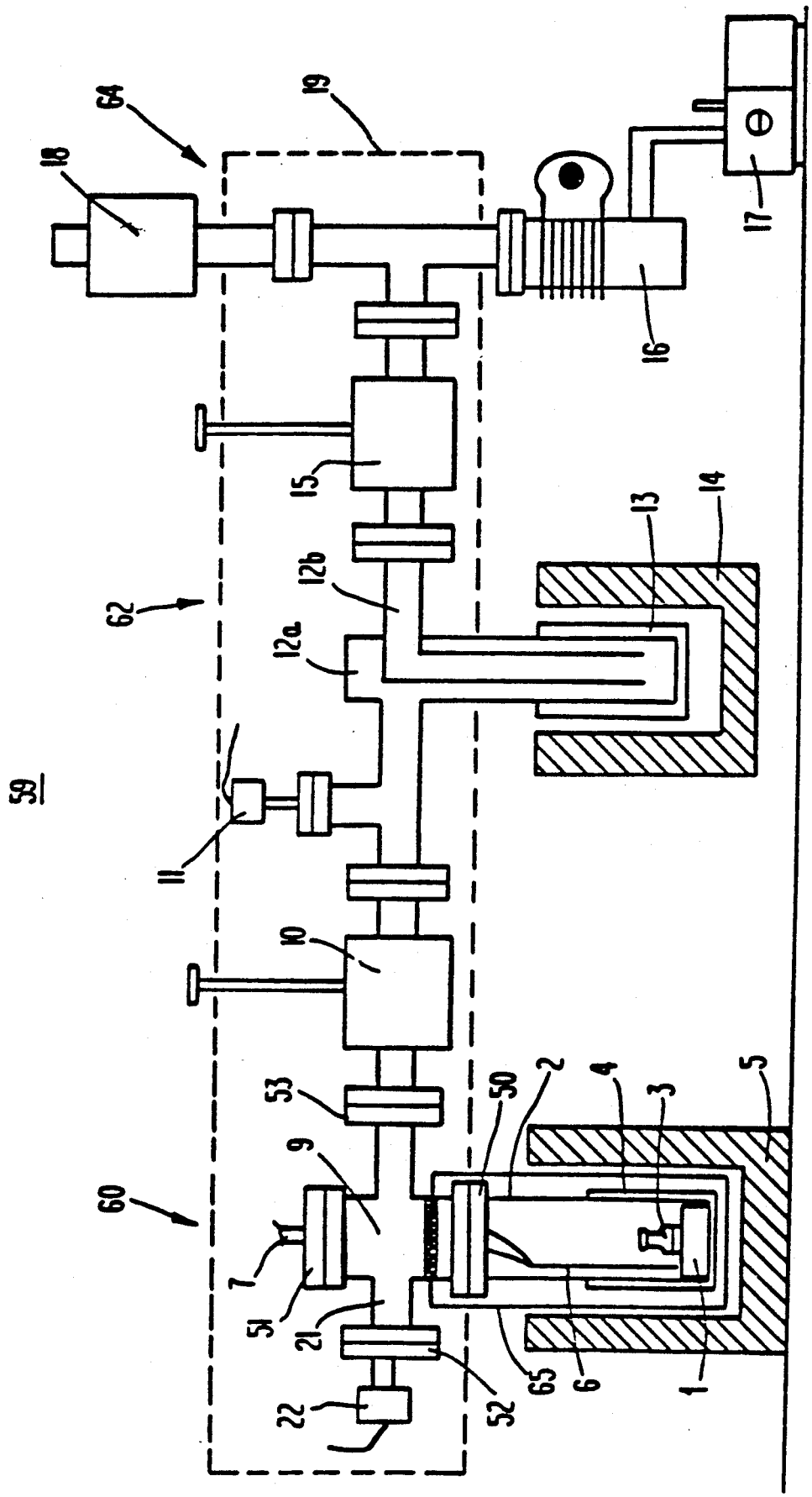
FIGS. 1a, b, are schematic views of the apparatus of the present invention.

Although specific forms of the invention have been selected for illustration in the drawings and the following descriptions drawn in specific terms for the purposes of describing these forms of the invention, this description is not intended to limit the scope of the invention which is defined in the appended claims.

A schematic representation of the apparatus 59 is shown in FIG. 1a. The apparatus 59 includes a sample section 60, a trap section 62 and a vacuum section 64. These sections are interconnected by valves 10 and 15 described more fully herein below.

Valve 15 is affixed to vacuum section 64 which includes a mechanical vacuum pump 17 and diffusion type vacuum pump 16. Vacuum section 64 also includes a high vacuum valve 18 which allows gas to be bled back into the system.

Valves 10, 15 and 18 are all of a high vacuum type capable of operating at pressures less than $10^{-6}$ Torr to be created within the apparatus 59. Other pumping systems may also be employed. Accordingly, all fittings and materials employed are selected to allow operation at such low pressures with an acceptable margin of safety.

The sample section 60 includes a sample holder 1 adapted to receive an open vessel 3 containing a solid sample to be tested. The sample holder 1 rests on the bottom of a detachable vacuum chamber 2. Extending into the vacuum chamber 2 adjacent the sample vessel 3, is a thermocouple 6 attached to appropriate apparatus (not shown) by wire leads 7. Thermocouple 6 allows determination of the temperature of the sample within vacuum chamber 2.

Means for heating the vacuum chamber 2 is provided. Preferably, the heating means comprises an electrical resistance heating unit 4 affixed to the exterior of vacuum chamber 2. Vacuum chamber 2 is oriented in a Dewar flask 5 with sufficient space between the vacuum chamber 2 and the Dewar flask 5 to allow a cooling liquid to be placed therein.

The vacuum chamber 2 is releaseably affixed to a "cross fitting" 9 as at flange 50. The wire leads 7 of thermocouple 6 extend through a second flange 51 on fitting 9. A third flange 52 of fitting 9 has a pressure sensor 22 affixed thereto to measure the pressure within vacuum chamber 2. The fourth flange 53 of fitting 9 is affixed to a valve 10 oriented between the sample section 60 and trap section 62. Valve 10 allows the sample section 60 to be isolated from trap section 62.

Trap section 62 comprises an inlet 12a from valve 10 connected to a vessel 13 having an outlet 12b. Vessel 13 is oriented in a second Dewar flask 14. Oriented in inlet 12a of vessel 13 is a pressure sensor 11 to measure the pressure within a trap section 62. The outlet 12b of vessel 13 is affixed to a second valve 15 which in combination with valve 10 allows trap section 62 to be isolated. Vessel 13 includes means for heating the vessel, preferably comprising an electrical resistance heating unit 113 affixed to the exterior of trap vessel 13.

Preferably, the vacuum chamber 2, trap 13 and all fittings and pipes are constructed of stainless steel. In order to avoid undesirable leaks, all fittings and flanges preferably employ copper or other suitable gaskets.

A secondary heating system, indicated by dashed line 19, may be provided around valves 10, 15 and the related fittings as described in more detail herein below.

Figure 1B:
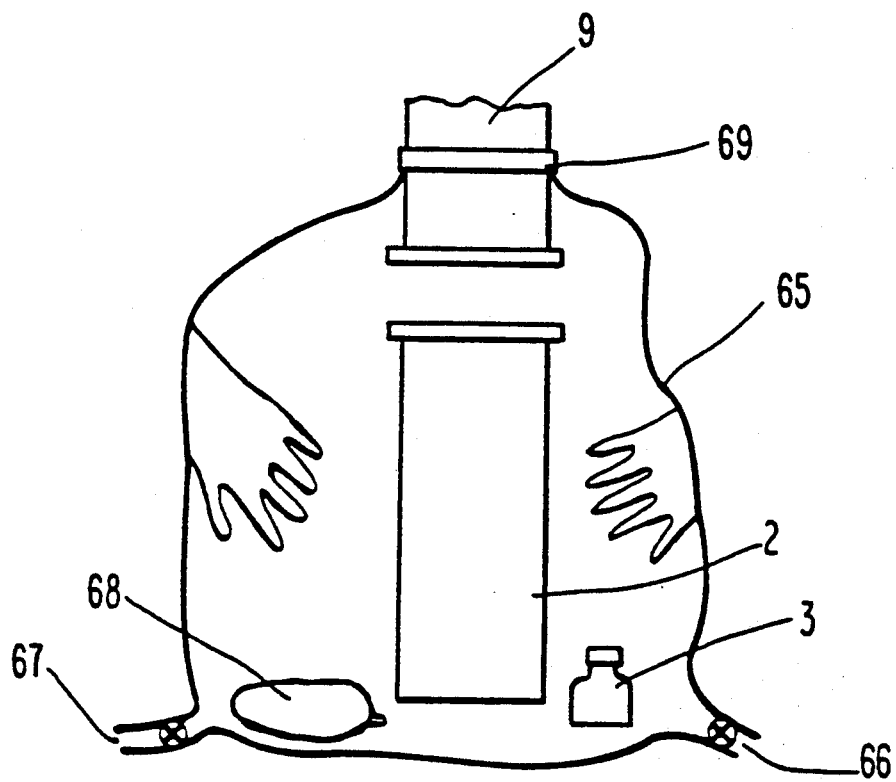

Referring now to FIG. 1b, there is shown the preferred embodiment of apparatus 59 wherein transfer of a moisture sample to the vacuum chamber 2 is accomplished using a commercially available sealable plastic glove bag 65. The bag 65 is clamped around fitting 9 and has a large opening to permit items to be loaded into the bag 65 prior to sealing the bag 65 to the metal cross 9. All tools, samples, etc. must be placed within bag 65 before sealing.

Additionally, a small helium or hydrogen filled balloon 68 is enclosed in glove bag 65. Balloon 68 has a buoyancy within bag 65 in accordance with the relative weights and concentrations of the inert gas and atmospheric air within bag 65. Connections 66 and 67 are used for filling and emptying the bag of helium or hydrogen in order to perform the method of the present invention for determining moisture content in an inert environment. Using connections 66, 67 the inert gas is added to bag 65 and released repeatedly until balloon 68 no longer floats within bag 65 thereby indicating that the concentration of the inert gas within bag 65 is approximately equal to the concentration within balloon 68. This method for determining the concentration of inert gas within bag 65 using the buoyancy of balloon 68 can be used for both helium and hydrogen.

In operation, the apparatus of the present invention is employed to determine the moisture content of a sample. The sample size is preferably 1 mg or larger. The sample contained in container 3, the sample holder 1, the metal gasket for flange 50, tools for connecting flange 50 to cross 9 and the helium or hydrogen filled balloon 68 are loaded into the glove bag 65. The glove bag is purged of atmospheric gases by filling and releasing the selected gas through connectors 66 and 67 as previously described. Completion of replacement of the atmospheric gases in bag 65 is indicated by the helium or hydrogen balloon 68 resting on the bottom of bag 65 as also previously described.

With valves 10 and 15 in an open position and the vacuum pumps 16 and 17 in an off position, the entire system is pressurized to one atmosphere with either helium or hydrogen by opening valve 18. Valve 10 is now placed in a closed position isolating the chamber 2 from the rest of the system. Flange 50 is then disconnected from cross fitting 9 and valve 18 is closed. The sample is placed in container 3 and container 3 is oriented on sample holder 1. Valve 18 is closed, thereafter, thermocouple 6 is attached to the sample holder 1 which is thereafter oriented in vacuum chamber 2. The seal from sample contained 3 is removed just prior to connecting flange 50 to the cross 9. Vacuum chamber 2 is then fixed to fitting 9. The helium or hydrogen gas is released from the glove bag 65 and the bag is detached from cross 9. The temperature of vacuum chamber 2 is then decreased to below $-150°$ C. and preferably to about $-195°$ C. by placing liquid nitrogen in Dewar flask 5. The temperature is monitored by the output of thermocouple 6.

By lowering the temperature of the sample to below $-150°$ C. or lower, the accuracy of the moisture determination is increased by effectively eliminating moisture loss from the sample during pumping as described below because very few molecules of water can escape from the surface of the ice at this very low temperature.

When the sample is at the desired temperature of below $-150°$ C., and valves 10 and 15 are open, mechanical pump 17 is energized and the pressure within the apparatus is reduced to approximately $5\times10^{-2}$ Torr. Valve 10 is again placed in a closed position. Thereafter, diffusion pump 16 is energized and the system pressure is reduced to less than $1\times10^{-5}$ Torr. Thus this method removes all moisture from trap section 62 which is at ambient temperature without adding any moisture to the sample 3 which is at $-195°$ C. Removal of moisture from the system can be accelerated by energizing heater 19 and trap heater 113.

Thereafter, the moisture in the sample is transferred to the trap 13 as follows. Valve 10 is placed in an open position and the pressure in the system is lowered to less than $1\times10^{-6}$ Torr. Heater 113 is turned off and the temperature in vessel 13 is decreased to below $-150°$ C. and preferably below $-195°$ C. by placing liquid nitrogen in Dewar flask 14. Heater 19 remains on to prevent moisture from collecting on the walls of the system. Dewar flask 5 around vacuum chamber 2 is removed and vacuum chamber 2 is heated by energizing heater 4. The temperature of the sample in vacuum sublimation is effectively eliminated. The sample is held at a predetermined temperature, for example, at $+20°$ C/ This temperature can be in the range of $+4°$ C. to $+250°$ C. The sample is held at this temperature until the system pressure, as measured by pressure sensor 11, is less than $1\times10^{-5}$ Torr thereby indicating the end of moisture released from the sample.

Thereafter, valves 10 and 15 are closed isolating the moisture from the sample in the trap section 62. Dewar flask 14 is removed and the trap vessel 13 is heated by energizing the trap heater 113 until the temperature is in the range of $+70°$ C. to $+100°$ C. The increase in pressure, as measured by pressure sensor 11 is a direct measure of the amount of water removed from the sample.

In measuring the moisture of a gas sample, the gas is charged to vacuum chamber 2. Vacuum chamber 2 is cooled to below $-150°$ C. causing moisture to condense and freeze on the walls of vacuum chamber 2. The system is then evacuated by vacuum pumps 16, 17 to a pressure of less than $1\times10^{-5}$ Torr. Vacuum chamber 13 is chilled $-195°$ C. after the Dewar flask 5 is removed and vacuum chamber 2 is heated by energizing heating element 4 to heat vacuum chamber 2 near 100° C. After the pressure becomes less than $1\times10^{-5}$ Torr, valves 10, 15 are closed and trap 13 is heated. The increase in system pressure as measured by pressure sensor 11 is a direct measure of the amount of moisture that was in the gas.

Using the vapor pressure of ice as a standard since the volume of the system is known, the system can be calibrated by providing a known pressure To perform this calibration a sufficient water is added to the sample holder 1 to give a fill height of 0.5 cm. A thermocouple is attached to the container such that the thermocouple junction is below the surface of the water. The water is frozen to at least $-150°$ C. and even to $-190°$ C. and the entire system evacuated to less than $1\times10^{-6}$ Torr.

Oven 19 is then turned on and the system and trap 13 are heated to between 70° C. and 100° C. in order to get the apparatus and the gauge to approximately the same temperature. The c pressure sensor 11 of the apparatus is then zeroed.

Heat is applied to the ice by means of heater 4 in order to increase the temperature of the ice. At a given ice temperature valve 15 is closed and valve 10 is opened. From the vapor pressure of the ice at the given temperature, the volume and temperature of the system between valves 10, 15, the relationship between the amount of water vapor in the gas phase and pressure gauge reading can be determined. This method of calibration can be repeated many times and the standard deviation can be determined in order to provide precision.

The system is shut down by deactivating vacuum pumps 16, 17 and allowing the system to reach ambient temperatures. Pressure and temperature sensor 6, 11 and 22 are turned off and release valve 18 is opened to allow the system pressure to return to ambient.

The apparatus of the present invention may be easily modified to determine not only the total moisture in a sample, as described above, but also to determine the desorption energy from the rate at which moisture is desorbed from the sample from a plot of log (dn/dt) verses 1/T. The desorption energy of the water vapor can be used to determine whether the water is surface moisture or chemically bonded water. Also, by observing the decrease in rate of desorption verses time, the total remaining moisture in the sample can be accurately estimated by extrapolation.

Figure 2:
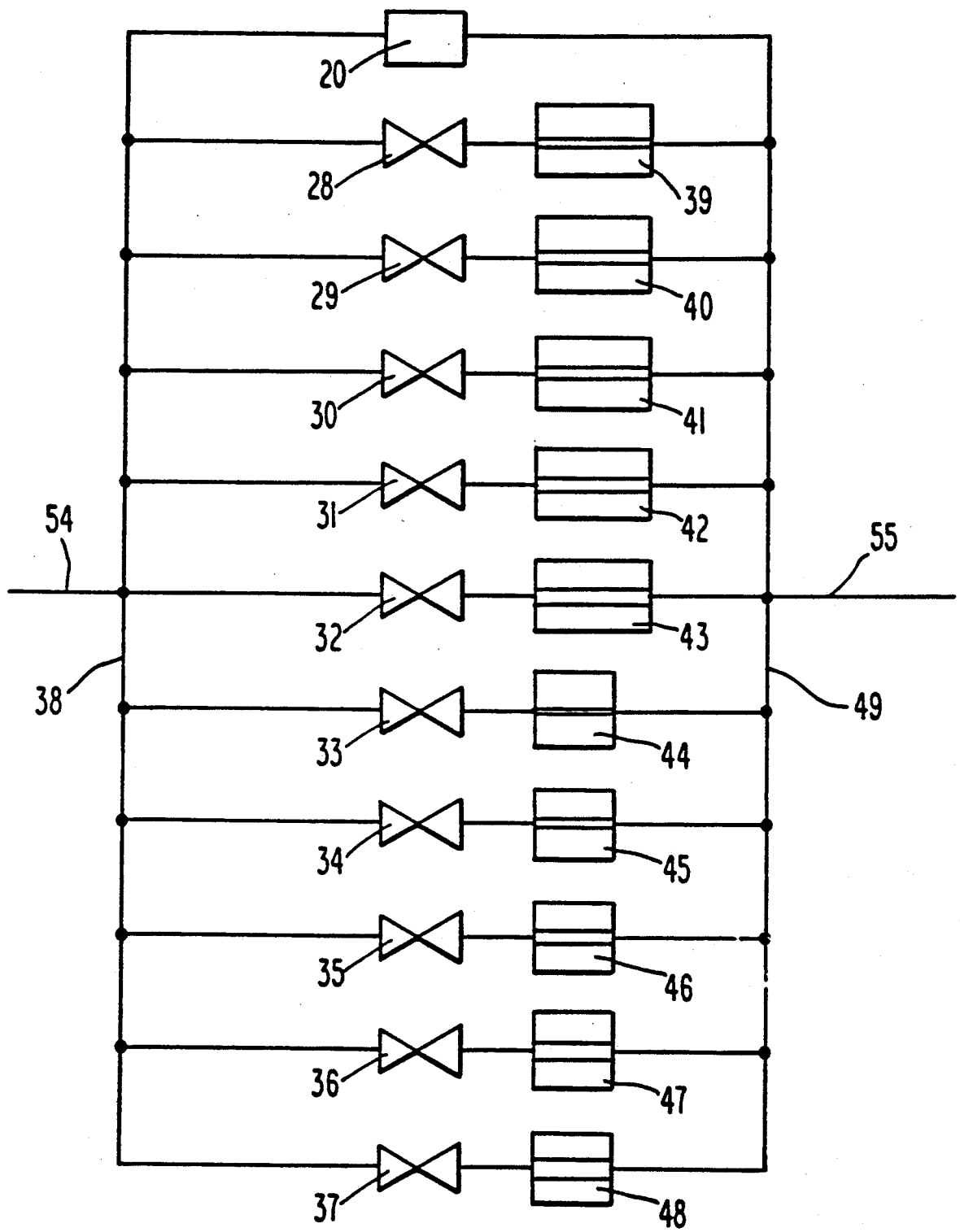
FIG. 2 is a schematic representation of the gas conductance apparatus of the present invention.

FIG. 2 is a view of a schematic of an apparatus employed to determine moisture flow rate, or conductance, from the sample. The apparatus comprises an inlet 54 and an outlet 55. The apparatus is oriented in FIG. 1 between cross fitting 9 and valve 10 at flange 53 with inlet 54 oriented toward fitting 9 and outlet 55 oriented towards valve 10.

Inlet 54 leads to a first manifold 38 and outlet 55 is connected to a second manifold 49. Extending, in parallel, between manifolds 38 and 49 are a bypass valve 20 and a plurality of electrically operated valves 28 to 37 and conductance tubes 39-48 respectively. The conductance tubes 39-48 comprise tubes having an orifice of known bore diameter and length which will transmit a known volume of gas at a known pressure drop across the tube. The conductant F of each tube is varied as follows: $39=1$ F; $40=2$ F; $41=3$ F; $42=4$ F; $43=5$ F; $44=10$ F; $45=20$ F; $46=30$ F; $47=40$ F; and $48=50$ F. Thus, by appropriate manipulation valves 28-37 are closed and valve 20 is opened when the system is being evacuated after the sample has been cooled to $-195°$ C. Prior to moisture transfer from the sample section 60 to trap section 62, valve 20 is closed. Thereafter, valves 28-37 are manipulated during moisture transfer such that the pressure in the sample section, as measured by pressure sensor 22 is held constant. The gas flow rate as a function of time, for a given trap 13 pressure can then be determined by recording which valves 28-37 are opened in order to maintain a constant pressure in chamber 2. In this manner, the energy of the desorption can be determined throughout the entire moisture analysis by plotting log (dn/dt) as a function of 1/T where dn/dt is the rate of desorption and the temperature T of the sample is expressed in degrees Kelvin. Also, by observing the decrease in the rate of desorption verses time, the remaining moisture in the sample can be estimated by extrapolation.

It should be understood that the foregoing description and drawings of the invention are not intended to be limiting, but are only exemplary of the invented features which are defined in the claims.

What is claimed is:

1. A method of determining the amount of moisture in a sample comprising the steps of:
   (a) placing a sample in a sealed vacuum chamber having an inert gas environment;
   (b) reducing the temperature in said vacuum chamber to below about $-150°$ C.;
   (c) connecting said vacuum chamber to a moisture trap;
   (d) reducing the pressure in said vacuum chamber and said moisture trap to below about $1 \times 10^{-5}$ Torr;
   (e) reducing the temperature in said moisture trap to below about $-150°$ C.;
   (f) heating said vacuum chamber to between $+40°$ C. and $+250°$ C., thereby causing a change in pressure in said vacuum chamber and said moisture trap;
   (g) isolating said moisture trap when a relatively constant pressure is reached; and
   (h) heating said isolated moisture trap and recording an indication of pressure change in said moisture trap as an indication of the amount of moisture removed from the sample, whereby moisture loss from the sample during steps a-f is effectively eliminated by the use of extremely low temperatures during steps (b), (e) and extremely low pressure in step (d).

2. The method of claim 1, wherein the temperature in said vacuum chamber is reduced to the temperature of liquid nitrogen.

3. The method of claim 1, wherein said moisture trap is heated as the pressure is reduced in step (d).

4. The method of claim 1, wherein the temperature in said moisture trap is reduced in step (e) to about the temperature of liquid nitrogen.

5. The method of claim 1, wherein said isolated moisture trap is heated in step (h) to about 100° C.

6. The method of claim 1, wherein said inert gas is hydrogen.

7. The method of claim 1, wherein said inert gas is helium.

8. The method of claim 1, wherein step (f) comprises heating said vacuum chamber to about 100° C.

9. A process for analyzing the moisture content in a sample comprising the steps of:
   (a) isolating the sample comprising moisture in a vacuum chamber having an inert gas environment;
   (b) reducing the temperature in said vacuum chamber to below about $-150°$ C.;
   (c) linking said vacuum chamber to a moisture trap;
   (d) reducing the pressure in said vacuum chamber and said moisture trap to below about $1 \times 10^{-5}$ Torr;
   (e) reducing the temperature in said moisture trap to below about $-150°$ C.;
   (f) heating said vacuum chamber to about 100° C. thereby effecting the transfer of moisture from said vacuum chamber to said moisture trap;
   (g) isolating said moisture trap; and
   (h) heating said isolated moisture trap while measuring change in pressure therein, thereby determining the amount of moisture removed from the sample, whereby moisture loss from the sample during steps a-f is effectively eliminated by the use of extremely low temperatures during steps (b), (e) and extremely low pressure in step (d).

10. The process of claim 9, wherein the temperature in said vacuum chamber is reduced to the temperature of liquid nitrogen.

11. The process of claim 9, wherein said moisture trap is heated as the pressure is reduced in step (d).

12. The process of claim 9, wherein the temperature in said moisture trap is reduced in step (e) to the temperature of liquid nitrogen.

13. The process of claim 9, wherein step (f) comprises heating said vacuum chamber to about 100° C.

14. Apparatus for analyzing the moisture content in a sample which comprises:
   (a) a sample receiving vacuum chamber including means to selectively cool said vacuum chamber to below about $-150°$ C. and means to heat said vacuum chamber;
   (b) means for providing an inert gas environment surrounding a sample within said chamber;
   (c) a moisture trap, selectively linked in series with said vacuum chamber, said moisture trap including means to selectively cool said moisture trap to below about $-150°$ C. and means to heat said moisture trap;
   (d) pressure reducing means selectively connected in series with said moisture trap to selectively reduce the pressure in said vacuum chamber and said moisture trap to below about $1 \times 10^{-5}$ Torr;
   (e) means to isolate said moisture trap from said vacuum chamber and said pressure reducing means;
   (f) means to isolate said vacuum chamber; and
   (g) means to measure sample temperature means to measure pressure in said vacuum chamber and means to measure pressure in said moisture trap.

15. The apparatus of claim 14, wherein said vacuum chamber is a stainless steel chamber having an electrical resistance heating element affixed thereto and is oriented in a Dewar flask.

16. The apparatus of claim 14, wherein said moisture trap includes an electrical resistance heating element affixed thereto and is oriented in a Dewar flask.

17. The apparatus of claim 14, wherein said pressure reducing means comprises a combination of mechanical and diffusion vacuum pumping means.

18. The method of claim 1, wherein the pressure is reduced in step (d) by exerting an evacuating pressure of below about $1 \times 10^{-5}$ Torr by an evacuating means linked to said moisture trap, and said evacuating pressure is maintained until said moisture trap has been isolated in step (g).

19. The method of claim 2, wherein the temperature in said moisture trap is reduced in step (e) to about the temperature of liquid nitrogen.

20. The method of claim 19, wherein said isolated moisture trap is heated in step (h) to about 100° C.

21. The method of claim 20, wherein the pressure is reduced in step (d) by exerting an evacuating pressure of below about $1 \times 10^{-5}$ Torr by an evacuating means linked to said moisture trap, and said evacuating pressure is maintained until said moisture trap has been isolated in step (g).

22. The process of claim 9, wherein said isolated moisture trap is heated in step (h) to about 100° C.

23. The process of claim 9, wherein the pressure is reduced in step (d) by exerting an evacuating pressure of below about $1\times10^{-5}$ Torr by an evacuating means linked to said moisture trap, and said evacuating pressure is maintained until said moisture trap has been isolated in step (g).

24. The process of claim 10, wherein the temperature in said moisture trap is reduced in step (e) to about the temperature of liquid nitrogen.

25. The process of claim 24, wherein said isolated moisture trap is heated in step (h) to about 100° C.

26. The process of claim 25, wherein the pressure is reduced in step (d) by exerting an evacuating pressure of below about $1\times10^{-5}$ Toor by an evacuating means linked to said moisture trap, and said evacuating pressure is maintained until said moisture trap has been isolated in step (g).

27. The process of claim 9, wherein the water vapor gas conductance is measured during the transfer of moisture from said vacuum chamber to said moisture trap in step (f).

28. The process of claim 9, wherein the rate of desorption of the moisture is determined during the transfer of moisture from said vacuum chamber to said moisture trap in step (f).

29. The process of claim 28, wherein the pressure in said vacuum chamber is maintained relatively constant after heating of said vacuum chamber has been initiated.

30. The process of claim 9, wherein the energy of desorption of the moisture is determined during the transfer of moisture from said vacuum chamber to said moisture trap in step (f).

31. The process of claim 30, wherein the energy of desorption is determined by using the rate of desorption of the moisture and the temperature in the vacuum chamber during the transfer of moisture from said vacuum chamber to said moisture trap in step (f).

32. The process of claim 31, wherein the pressure in said vacuum chamber is maintained relatively constant after heating of said vacuum chamber has been initiated.

33. The process of claim 9, wherein it is determined whether the moisture being transferred at a given moment during step (f) is surface moisture or chemically bonded moisture.

34. The process of claim 33, wherein said determination is made by first determining the desorption of the moisture being transferred during step (f).

35. The process of claim 9, wherein the amount of moisture remaining in said vacuum chamber after the transfer of moisture has been initiated in step (f) is determined.

36. The process of claim 35, wherein said determination is made by first determining changes in the rate of desorption and extrapolating the amount of remaining moisture therefrom.

37. The process of claim 36, wherein the rate of desorption is determined by monitoring the pressure in said vacuum chamber and in said moisture trap, the actuation of a plurality of valves oriented in series with an equal number of conductance tubes, each conductance tube having a known gas conductance, said valves and corresponding conductance tubes being oriented in parallel between said vacuum chamber and said moisture trap, as said valves are actuated in such a manner as to maintain a relatively constant pressure within said vacuum chamber during the transfer of moisture between said vacuum chamber and said moisture trap in step (f).

38. The apparatus of claim 14 further comprising a means to measure gas flow rate between said vacuum chamber and said moisture trap.

39. The apparatus of claim 38, wherein said means to measure gas flow rate comprises a plurality of valves oriented in series with an equal number of conductance tubes, each conductance tube having a known gas conductance, said plurality of valves and corresponding conductance tubes being oriented in parallel between said vacuum chamber and said moisture trap.

40. The apparatus of claim 38, further comprising a means to selectively bypass said means to measure gas flow rate.

41. The apparatus of claim 14, wherein:
said vacuum chamber is a stainless steel chamber having a electrical resistance heating element affixed thereto and is oriented in a Dewar flask;
said moisture trap includes an electrical resistance heating element affixed thereto and is oriented in a Dewar flask; and
said pressure reducing means comprises a combination of mechanical and diffusion vacuum pumping means.

42. The apparatus of claim 41, further comprising:
(g) a means to measure gas flow rate between said vacuum chamber and said moisture trap, said means to measure gas flow rate comprising a plurality of valves oriented in series with an equal number of conductance tubes, each conductance tube having a known gas conductance, said plurality of valves and corresponding conductance tube being oriented in parallel between said vacuum chamber and said moisture trap; and
(h) a means to bypass said means to measure gas flow rate.

* * * * *